(12) United States Patent
Balasubramaniam et al.

(10) Patent No.: US 10,073,065 B2
(45) Date of Patent: Sep. 11, 2018

(54) SEGMENTED STRIP DESIGN FOR A MAGNETOSTRICTION SENSOR (MSS) USING AMORPHOUS MATERIAL FOR LONG RANGE INSPECTION OF DEFECTS AND BENDS IN PIPES AT HIGH TEMPERATURES

(71) Applicant: INDIAN INSTITUTE OF TECHNOLOGY MADRAS, Channai (IN)

(72) Inventors: Krishnan Balasubramaniam, Channai (IN); Tarun Kumar Mishra, Channai (IN)

(73) Assignee: INDIAN INSTITUTE OF TECHNOLOGY MADRAS, Chennai (IN)

( * ) Notice: Subject to any disclaimer, the term of this patent is extended or adjusted under 35 U.S.C. 154(b) by 97 days.

(21) Appl. No.: 14/786,809

(22) PCT Filed: Apr. 10, 2014

(86) PCT No.: PCT/IN2014/000229
§ 371 (c)(1),
(2) Date: Oct. 23, 2015

(87) PCT Pub. No.: WO2014/192012
PCT Pub. Date: Dec. 4, 2014

(65) Prior Publication Data
US 2016/0069841 A1    Mar. 10, 2016

(30) Foreign Application Priority Data
Apr. 29, 2013   (IN) .......................... 1897/CHE/2013

(51) Int. Cl.
*G01N 29/04* (2006.01)
*G01N 27/82* (2006.01)
(Continued)

(52) U.S. Cl.
CPC .......... *G01N 29/2412* (2013.01); *B06B 1/08* (2013.01); *B06B 1/085* (2013.01); *G01N 29/04* (2013.01);
(Continued)

(58) Field of Classification Search
CPC .... G01N 29/2412; G01N 29/04; G01N 29/11; B06B 1/08; B06B 1/085; B06B 1/04; B06B 1/045
See application file for complete search history.

(56) References Cited

U.S. PATENT DOCUMENTS 4,100,809 A * 7/1978 Bobrov .................... B06B 1/04
                                                      73/609
5,892,162 A * 4/1999 Spinks .................. B06B 1/045
                                                    73/40.5 A

(Continued)

*Primary Examiner* — Helen Kwok
(74) *Attorney, Agent, or Firm* — Seyfarth Shaw LLP; Brian Michaelis (57) ABSTRACT

The invention relates to a continuous monitoring system which will monitor the pipes without the need of shutting down of the plants. The major issues in designing such a system using magnetostriction as per prior art is the loss of magnetization of the permanent magnets used to provide the magnetic bias and also the disbonding of interfaced adhesives with which the magnetostrictive ribbons are bonded at high temperatures. The invention identifies a novel sensor which can be taken up to high temperatures without any loss of signal strength, this is achieved by generating guided waves using a special amorphous magnetostrictive ribbons. L(0, 2) mode waves are generated using these ribbons to monitor pipes working at high temperatures as per the invention.

9 Claims, 12 Drawing Sheets

(51) Int. Cl.
*G01N 29/24* (2006.01)
*B06B 1/08* (2006.01)

(52) U.S. Cl.
CPC ............... *G01N 2291/023* (2013.01); *G01N 2291/0289* (2013.01); *G01N 2291/2634* (2013.01)

(56) References Cited

U.S. PATENT DOCUMENTS

| | | | | |
|---|---|---|---|---|
| 6,239,593 | B1* | 5/2001 | Burkhardt | G01B 7/24 324/209 |
| 6,393,921 | B1* | 5/2002 | Grimes | G01L 9/16 73/722 |
| 6,397,661 | B1* | 6/2002 | Grimes | G01K 7/38 324/207.13 |
| 6,429,650 | B1* | 8/2002 | Kwun | G01N 29/11 324/220 |
| 6,624,628 | B1* | 9/2003 | Kwun | G01N 29/11 324/240 |
| 2001/0022514 | A1* | 9/2001 | Light | G01N 17/006 324/240 |
| 2004/0095137 | A1* | 5/2004 | Kwun | G01N 29/2412 324/240 |
| 2009/0174399 | A1* | 7/2009 | Vinogrador | G01N 27/82 324/238 |
| 2010/0259252 | A1* | 10/2010 | Kim | B06B 1/085 324/240 |
| 2012/0091829 | A1* | 4/2012 | Choi | G01N 29/2418 310/26 |
| 2012/0119732 | A1* | 5/2012 | Rose | G01N 29/2412 324/240 |

* cited by examiner

SEGMENTED STRIP DESIGN FOR A MAGNETOSTRICTION SENSOR (MSS) USING AMORPHOUS MATERIAL FOR LONG RANGE INSPECTION OF DEFECTS AND BENDS IN PIPES AT HIGH TEMPERATURES

FIELD OF INVENTION

The invention relates to a sensor system for inspection of pipes working continuously at high temperature for flaw detection.

CROSS REFERENCE TO RELATED APPLICATIONS

This application is a national phase application under 35 U.S.C. § 371 of International Application No. PCT/IN2014/000229, filed on Apr. 10, 2014, which claims priority to Indian Patent Application No. 1897/CHE/2013, filed on Apr. 29, 2013; the disclosures of all of which are hereby incorporated by reference in their entirety.

BACKGROUND OF THE INVENTION

Many of the commercial pipelines in industries are insulated and operate at high temperatures. Currently, these pipes are inspected only during annual maintenance shutdown by stripping of the insulation. The insulation is then replaced after inspection at considerable costs. Inspection of pipes for flaw detection at high temperature has been a critical issue in many industries, especially nuclear and oil industries where shutdown of plants may incur heavy losses. Moreover, thermal shocks caused due to the shutdown may result in weakening of the pipe material and hence to avoid this slow cooling and heating rates are maintained, this slow cooling and heating may sometime take days.

Piping systems are often inspected ultrasonically to ensure safety. This can be accomplished by a series of point test but from outside the pipe. If insulation covers the pipe, as is often the case, access to pipe requires removal of the insulation to perform the test and then reinstallation when the test is complete. Removal and reinstallation of coating is not only time consuming but in most cases expensive too. There is therefore an urgent need for development of a quick, reliable method for the detection of cracks and corrosion under insulation. Long-range, longitudinal and torsional guided wave generated in pipes using Magnetostrictive sensors (MsS) have great potential for application to structural health monitoring of hard to inspect pipes.

The use of Guided waves had been an area of interest to many scientists particularly because of its immense capability in Long Range Ultrasonic Techniques (LRUT). This technique besides being cost effective is also very simplistic and user friendly. Guided waves usually refer to mechanical waves in ultrasonic frequencies that propagate in bounded medium (usually pipes and rods), these waves are confined within the geometries and are guided by geometric boundaries, and hence it is called as guided waves.

Generation of guided waves has taken place using piezoelectric principles or Magnetostrictive technology. Magnetostrictive Sensors (MsS) are used widely to monitor pipelines in industries. But, still the use of MsS at high temperatures remains a challenge. This is mainly because of the usual configuration used in the design of sensors.

Figure 1:
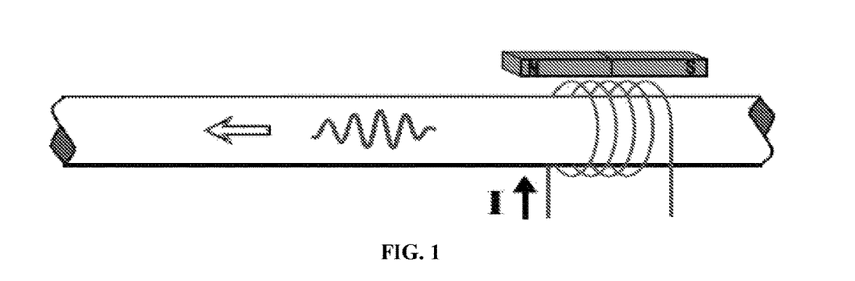
FIG. 1 is a schematic of a typical MsS sensor arrangement using magnets [1].

A typical MsS Technique employs the configuration as shown in FIG. 1. [1] MsS uses a "permanent magnet" to obtain the bias field and "adhesives" to bond the magnetostrictive tapes. These permanent magnets easily get demagnetized at very high temperatures which cause a loss in signal strength. The sandwiched adhesives interfaced between the pipe and magnetostrictive tape also get removed at high temperatures causing the delamination of sensors; thereby causing a large noise in the signals due to air coupling. The permanent magnets was considered essential in prior art because of the high value of bias required in the currently used Fe—Co strips in MsS Sensors.

The basic principle behind obtaining guided wave using MsS is the phenomenon called magnetostriction. The magnetization forces and magnetostrictive forces both operate to give rise to guided wave propagation. The latter one of these two is the usual force only in ferromagnetic materials. Since, all our study for this invention is mainly on mild steel pipes which are ferromagnetic, though the invention is not limited to this;

Magnetization Force Mechanism: Magnetization forces occur only in ferromagnetic Materials. The grains present in the material act as magnetic dipoles. In the presence of a biasing magnetic field, these dipoles tend to align in a direction and create magnetization inside the material. When an oscillating magnetic field is applied through the excitation coil, these magnetic dipoles experience force. This oscillating body force results in the propagation of acoustic waves inside the material. An equation given by Thompson [3] for this force is $$fM = \mu(M_O \cdot \nabla)H$$

Here, $f_M$=Force due to magnetization.
$M_O$=Magnetization vector of ferromagnetic material.
H=Magnetic field.
µ=Magnetic Permeability.

Magnetostriction Force Mechanism: A normalized dimensional change due to application of external magnetic field depending on the direction and magnitude of the field is called magnetostriction. It originates from the very fact that all main interactions between the atomic magnetic moments in solids depend on the distance between them (e.g. exchange interaction, dipole-dipole interaction, interaction of magnetic moments with crystal electric field). Here we will deal with only two kinds of magnetostriction effects. One is Joules effect used in transmission of waves and the other is Villari effect used in receiving of signals.

Thus, the main object and other objects of the invention is to obtain a good magnetization and magnetostrictive force from a material which has a capability to align its dipoles at very low bias field, or a material that has a very steep linear region in magnetostrictive curve and at the same time should possess a good magnetostriction constant.

SUMMARY OF INVENTION

The invention relates to a continuous monitoring system which will monitor the pipes without the need of shutting down of the plants. The major issues in designing such a system using magnetostriction as per prior art is the loss of magnetization of the permanent magnets used to provide the magnetic bias and also the disbonding of interfaced adhesives with which the magnetostrictive ribbons are bonded at high temperatures. The invention identifies a novel sensor which can be taken up to high temperatures without any loss of signal strength, this is achieved by generating guided waves using a special amorphous magnetostrictive ribbons.

L(0, 2) mode waves are generated using these ribbons to monitor pipes working at high temperatures as per the invention.

DESCRIPTION OF INVENTION

The present invention uses an amorphous material (Metglas) to generate pure modes of ultrasonic guided waves within long pipelines. Though the generation and use of non-dispersive T(0,1) mode has been widely exploited in prior art, but the dispersive modes like L(0,2) still have not been researched well. The dispersive modes have several advantages, particularly in corrosion defects, where the velocity of the mode changes with pipe wall thickness. The sensor as per the invention has. the capability of generating pure modes of both dispersive and non-dispersive nature. Therefore, it allows selection between both longitudinal and transverse modes depending on the major type of defects that has to be monitored. This system can thereby detect several types of defects in the pipe. By doing velocity-time calculations, one can identify the distance of potential damage in the pipe from the sensor. This sensor can work from subzero degrees up to 350° C. which is much higher than operable temperature in prior art. This makes the device a very potential and unique device useful to monitor pipelines that carry hot chemicals and fluids, in addition to normal pipelines.

It is proposed that the sensor be implemented in a structural health monitoring mode i.e. the sensor be permanently mounted on the pipes and the guided waves are generated in order to interrogate the health of the pipe during the serviceable life of the pipeline. Since the sensor is relatively simple in design as per the invention and has no moving parts or mechanisms that can fail, the robustness of the sensor is relatively high and hence can be used for industrial application.

The amorphous material so selected for use in the sensor of the invention for generating various modes has a very steep magnetostriction curve and therefore can be biased at very low magnetization. This magnetization is so low that for "ferritic" pipelines, applying 10 seconds of DC Bias using a biasing coil is sufficient for monitoring the pipe for at least two days. Since, there is no dependency on magnets or DC bias after magnetizing the pipe, the pipe can be monitored up to very high temperatures, without any reduction in signal amplitude.

Since, the waves are generated at lower frequency (about 50-70 kHz) the attenuation of signals is not much even at longer distances and therefore the waves can travel long distance, giving it the capability for long range pipe inspection.

Figure 2:
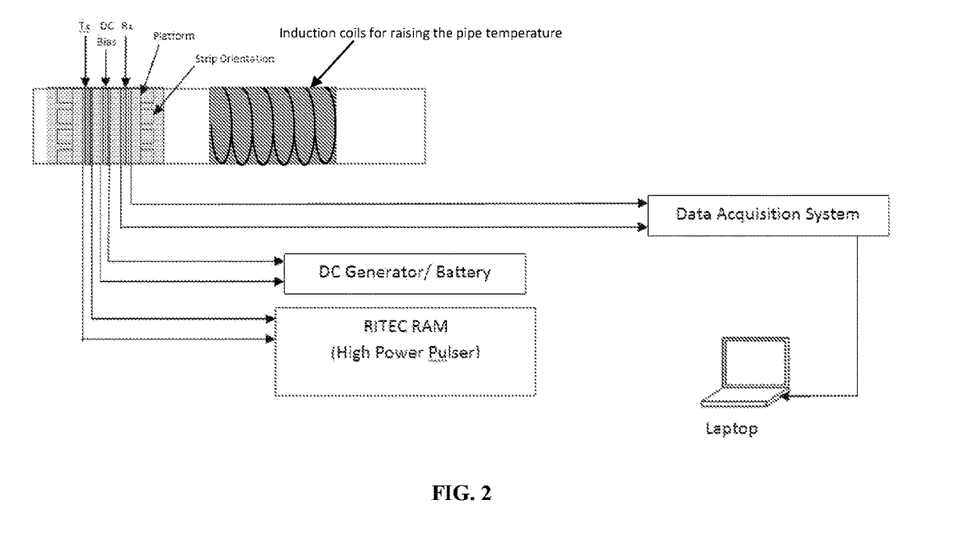
FIG. 2 is a schematic of an apparatus for inspection of pipes using L(0,2) mode at high temperatures using the sensor according to aspects of the present disclosure.

A typical sensor design as per the invention involves (1) arranging circumferentially, a plurality of spaced Segmented Amorphous strips on the piper surface for wave generation around and/or along the pipe. Some strips are placed maybe along the longitudinal axis of pipe and some maybe wound around the pipe. (2) Over these amorphous strips there shall be a common platform which may be typically made of motor winding sheet but not limited by this disclosure but this sheet is preferred as it is capable of withstanding high temperatures. Three coils are wound on a single platform surrounding the pipe to provide the excitation signal, a DC Bias and the reflected signal is also received from the same platform. (3) A platform is a typical base matching the geometry of the pipe on which the coils shall be wound. A silicon sheath cover on top is provided as protective cover to sensor at high temperatures (4) A data acquisition system to see and analyze the reflected signal is also provided. Hence the entire system is a single transducer system eliminating independent transmitters and receivers used in prior art. Generally one or more sensors along the length of the pipe line are placed for detection of flaws. The novelty of this invention lies in the unitary device which acts as single unitary transducer. The single transducer is capable of being used for excitation as well as receiving. The typical sensor is depicted in FIG. 2.

Figure 4:
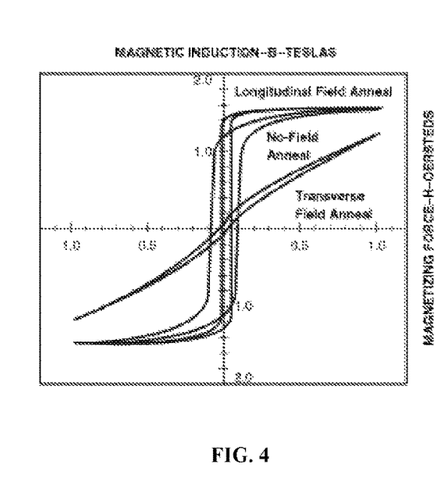
FIG. 4 shows DC hysterisis loop of 2605SA1 from Metglas® (Longitudinal field anneal material is used).

With a wide research for the correct material it was found, that amorphous ribbons of Fe with some alloys of B and Si must be considered as most preferred material to satisfy all the required parameters. Thus, an amorphous ribbon 2605SA1 (Iron-based) obtained from a commercial company Metglas and experiments were carried out. The following are the specifications of the material used for the MsS sensor. [3] FIG. 4 depicts the Hysterisis curve for this material
Saturation Magnetostriction (ppm): 27
Curie temperature (° C.): 399
Thickness (mils): 1.0

Figure 3A:
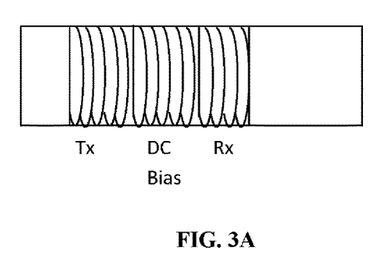
FIG. 3A is a schematic of coil arrangement for high temperature usage.
Figure 3B:
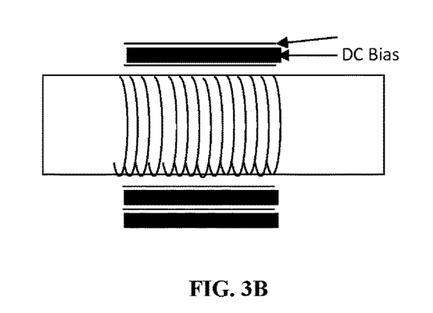
FIG. 3B is a schematic of coil arrangement for temporary DC Bias.

Two unique coil designs have been attempted in two embodiments for the sensor such that device can perform at high temperatures. In the first arrangement a single platform may have three coils arranged next to each other. The platform was then encapsulated in a silicon sheath capsule. In the second arrangement three coils are arranged on top of each other, with an insulation tape in between and then encapsulated. These designs make the sensor portable and usable at higher temperatures as a single composite device for inspection. (FIG. 3)

In one aspect of the invention the Transmitter coil was about 40 turns of 26 SWG copper wire, the receiver was 200 turns of 41 SWG and the DC Bias was 200 turns of 26 SWG. The sensor was made up of 8 cm strips of the above strips arranged such that the gap between two strips is 1 cm. For generating pure L(0,2) mode these strips are arranged in the longitudinal orientation, parallel to the axis of pipe. For torsional mode the strip are wound around the pipe. This is a conventional way of generating torsional mode.

It is very critical to choose the proper orientation of the MsS Strips to generate pure modes within the pipe. The spacing between the strip should be much less than $\lambda/2$. For example if speed of the wave measured is 5380 m/s at 67 kHz the spacing was chosen to be 10 mm.

Figure 5A:
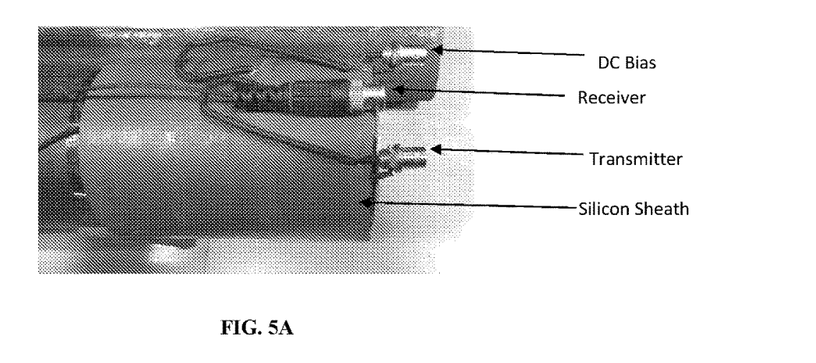
FIG. 5A shows the silicon sheath cover on the sensor.
Figure 5B:
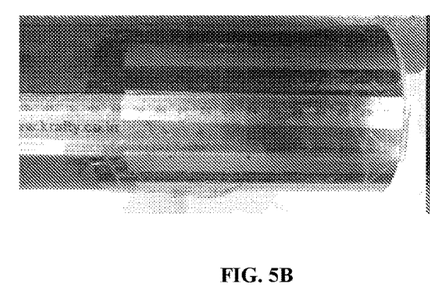
FIG. 5B shows the coils wound on the single platform.
Figure 5C:
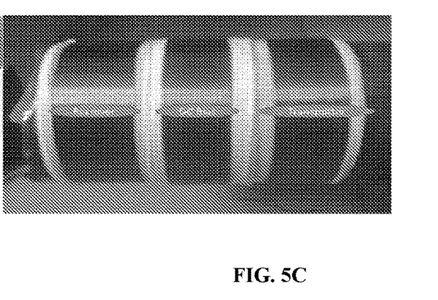
FIG. 5C shows the strip orientation for longitudinal mode wave generation.

Once the spacing is calculated the segmented strips are arranged in a symmetrical pattern with intermittent space between the strips around the pipe. Special care has to be taken to ensure that the strips are straight. Slight misalignment can lead to overlapping of various modes, leading to false alarms. These strips are placed and wound on the pipe using a common transparent tape thereby eliminating the use of adhesive. As such the strips are directly in contact with the pipe with no interfacing adhesive FIG. 5. No special adhesives are applied between the strips and pipe, as these adhesives can delaminate at higher temperatures.

The novelty of this invention is that after a very small initial bias it does not require any biasing in case of ferritic pipelines. However in case of non-ferrous pipelines continuous bias needs to be provided. This resolves the difficulty previously encountered in prior art by sensors working at high temperatures, which suffers permanent magnets getting demagnetized at such temperatures. None have attempted use of a segmented strip approach for generation of pure modes for the detection of defects and bends in pipes. Hence, this constitutes a novel technique for long range pipe inspection. The sensor does not involve any permanent magnets, couplant or adhesives as in usual MsS Sensors, therefore it can go up to 350° C. which is about 200° C. higher than the currently available MsS sensors. One other advantage of the new technique is that since no moving parts are involved in the sensor design, it is robust and can be used for many inspections. Lastly, the sensor of the invention operates at low frequency and therefore the attenuation of the signal is not much with distance, therefore the waves can travel long distances, up to 30 m on one side.

Figure 6:
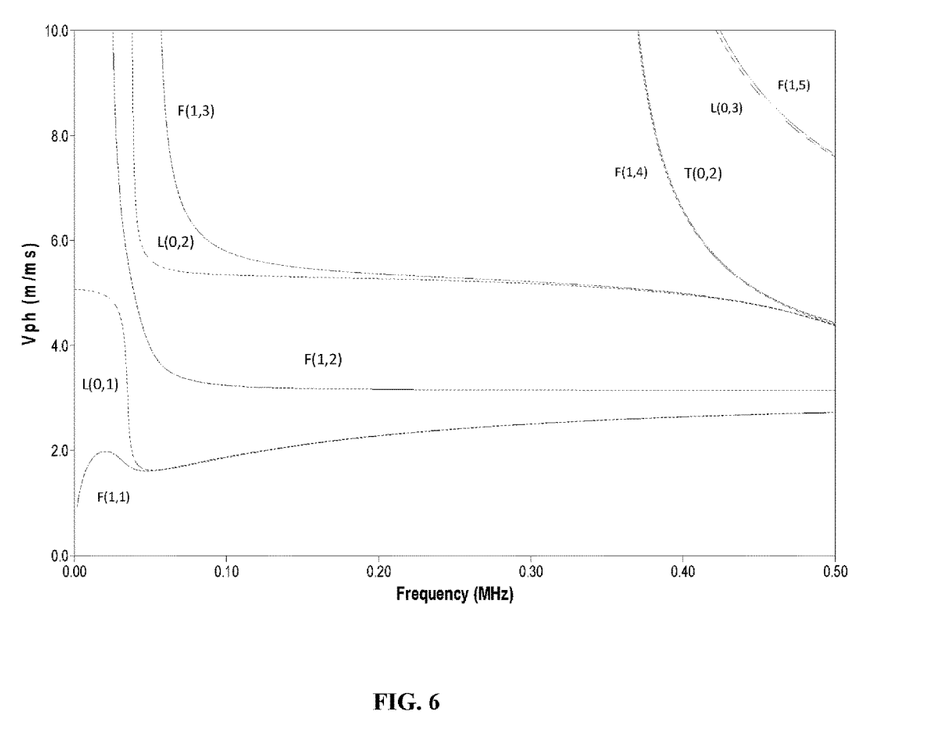
FIG. 6 is a disperse plot for MS tube sample (OD 50 mm; t 4.5 mm).

The mode generated was seen using a dispersion curve. A typical dispersion curve for 6 mm thick mild steel pipe was generated and can be seen in FIG. 6.

Figure 8:
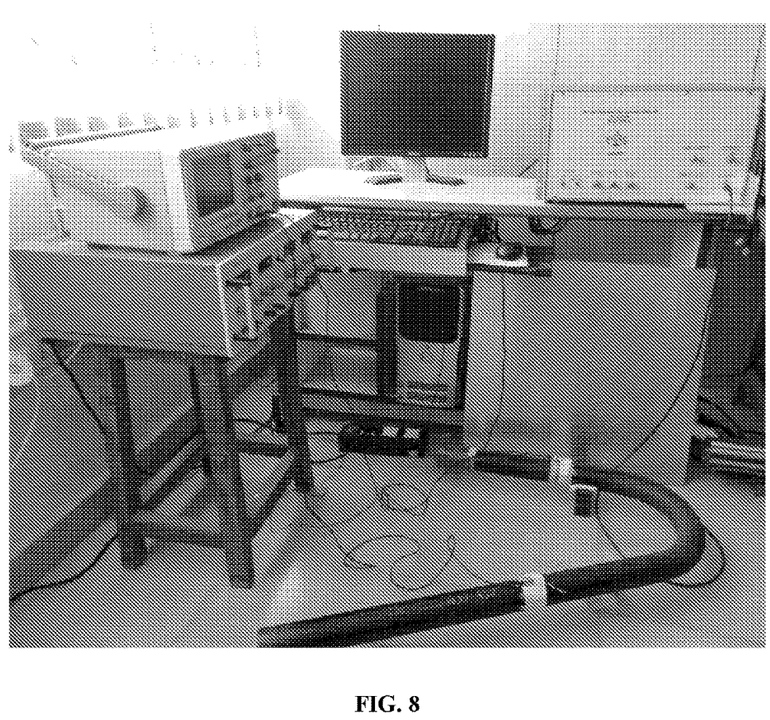
FIG. 8 shows an apparatus for monitoring bends in pipes using the MsS sensor.
Figure 9A:
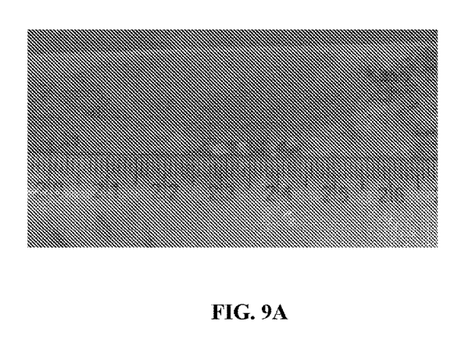
FIG. 9A shows a notch defect.
Figure 9B:
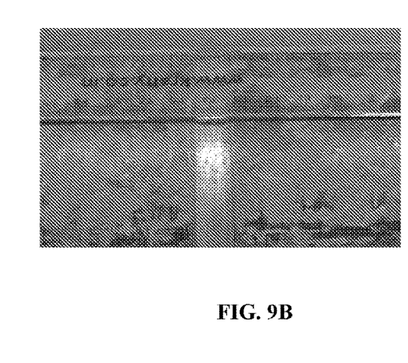
FIG. 9B shows a circumferential defect.
Figure 9C:
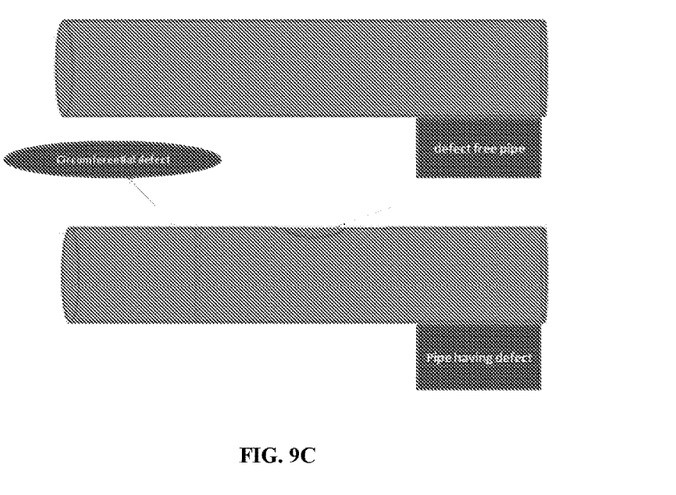
FIG. 9C is a schematic of a defect free pipe and a pipe having a defect, including a notch defect and a circumferential defect.
Figure 10A:
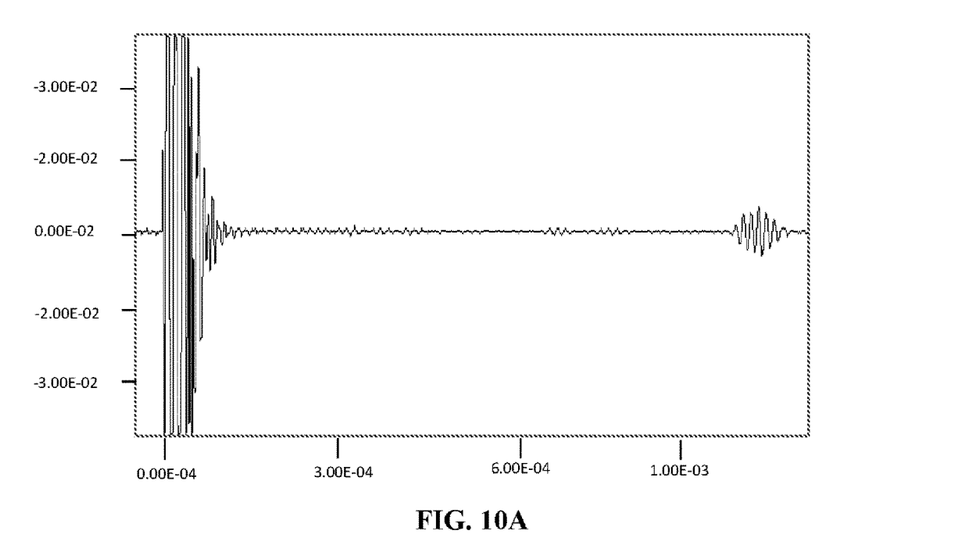
FIG. 10A shows the signal from a pipe without any defect.
Figure 10B:
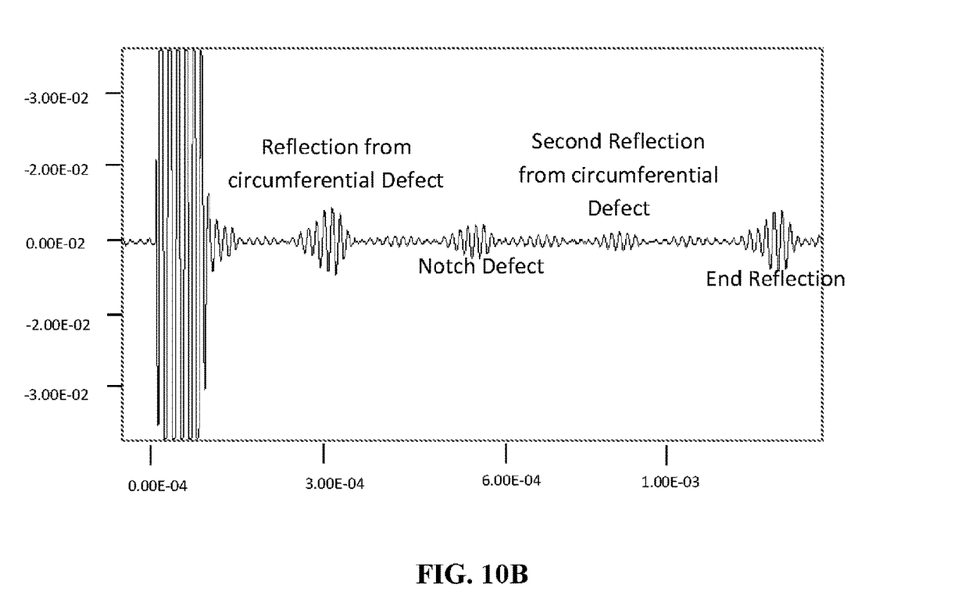
FIG. 10B shows the signal from a pipe with circumferential and notch defect.
Figure 11A:
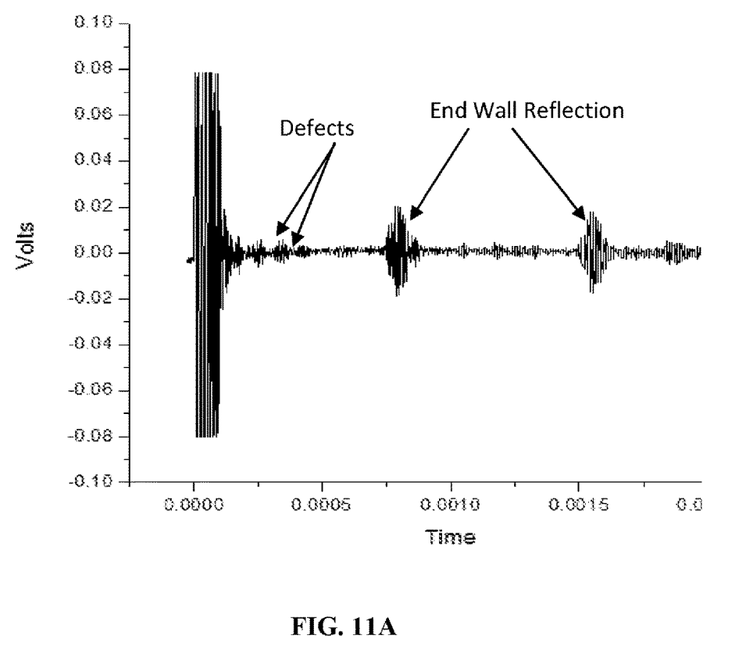
FIG. 11 shows signals for a pipe with defects at room temperature; (b) 100° C.; (c) 200° C.; and (d) 350° C.
Figure 11B:
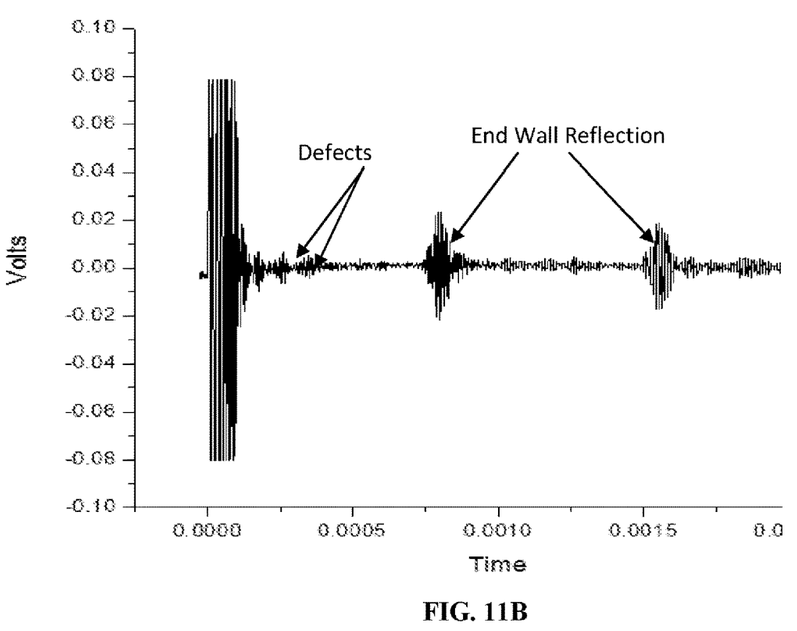
Figure 11C:
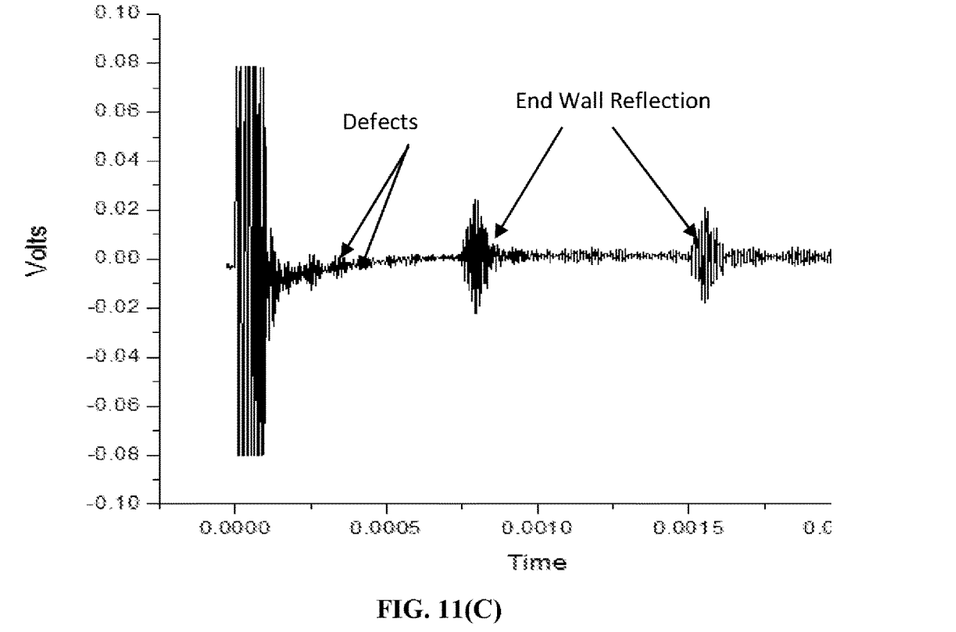
Figure 11D:
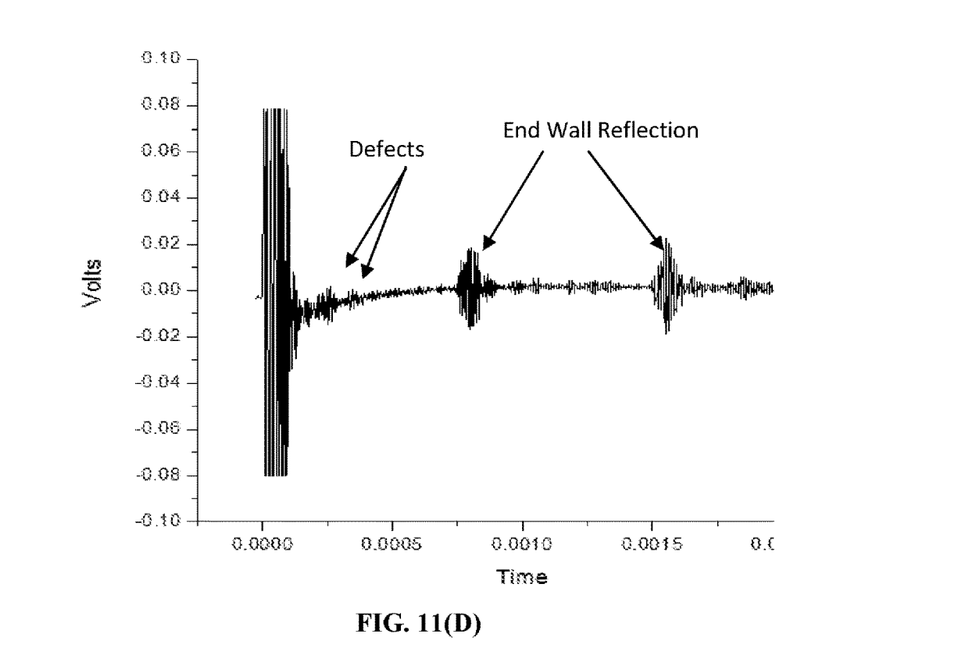

A typical apparatus for pipe inspection using the novel technique can be seen in FIG. 8. A Ritec Ram 5000 is used to give a 67 kHz tone burst signal to the transmitter, and a Data Acquisition system is employed to collect the reflected signal. A DC bias is given initially to magnetize the pipe but the bias is taken off, as the sensor has the capability of working at very low magnetic field.

The reflected signals can be monitored using a DAQ system, a Lab View program was written for this purpose. The signal can also be seen on an oscilloscope. No amplifiers have been employed other than the amplifier within the oscilloscope itself.

In one aspect, the pipeline inspection system with a magnetostrictive sensor is configured to be placed in contact with the pipeline. The system shall have a hollow base cylindrical platform adapted to be around the pipe. The shape is such it is having generally a matching geometry of the pipe. A set of segmented ultra sound magnetostrictive strips is securely arranged within the said platform. This arrangement enables generating a plurality of ultrasonic guided pure mode waves. These waves maybe an either longitudinal mode or a torsional mode. Further a set of coils are wound encircling on the said platform, a first excitation signal coil, a second reflection signal coil and a third DC bias coil, wherein the platform, strips and coils co-operatively work as a sensor. The system also has a data acquisition system with circuitry for determining and identifying the flow in the pipe on the basis of received signals from the said sensor.

In another aspect, the said system of claim 1 wherein the said three coils maybe arranged side-by-side juxtaposition along the said platform and in spaced relationship thereto.

In another aspect, the three coils maybe arranged concentrically layered on top of each other around the said platform with an insulation layer in between.

In another aspect, the invention includes arranging of a plurality of segmented magnetostrictive strips arranged circumferentially around the pipe, some orienting longitudinally along the pipe axis and some arranged around the pipe perpendicularly to the pipe axis.

In another aspect the invention includes arranging a plurality of segmented sensor strips arranged circumferentially all orienting longitudinally along the pipe axis In another aspect the invention includes arranging a plurality of longitudinal sensor strips arranged circumferentially all orienting perpendicularly to the pipe axis and wound encircling around the pipe.

In another aspect the invention includes segmented ultra sound magnetostrictive strip which are made of amorphous material having a very steep magnetostrictive curve.

In another aspect the invention includes having a preferred amorphous material as Fe with alloys of B and Si.

In another aspect the said strips may be additionally held in position on the said platform with any roll-on conventional tape capable of withstanding high temperature.

Typical Applications of the Invention
For Detection of Common Defects in Pipe, and High Temperature Test To test the capability of the sensor for detecting defects, different defects were artificially created on a pipe. The pipe was then monitored with and without defects and the signals were compared.

The defects incorporated were one circumferential defects and one notch, in the form of corrosion. All the defects were 50% CSI. The defects generated can be seen in FIG. 9. And the signals for straight pipe as well as the pipe with defects can be seen in FIG. 10.

The signals obtained clearly demonstrate the capability of the sensor to detect defects. The Second signal from circumferential defect occurs when the reflection from the circumferential defect interacts with the notch defect. This wave will reach the sensor before the end wall reflection.

The velocity of the wave was calculated and it was found to be 5380 m/s. The pipe used for inspection is 88 mm OD with 6 mm wall thickness.

Figure 7:
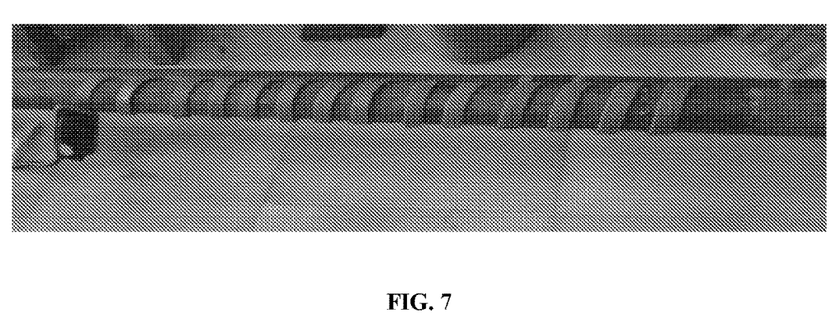
FIG. 7 shows heating coils wound around for high temperature inspection of pipes.

High Temperature Tests:

The temperature of a pipe with defects was increased using an induction coil wrapped around the pipe as shown in FIG. 7. The signals obtained are shown in FIG. 11. No major reduction in signal amplitude was observed for 350° C.

Typical Applications of the Invention

For Detection of Bends in Pipe

Figure 12:
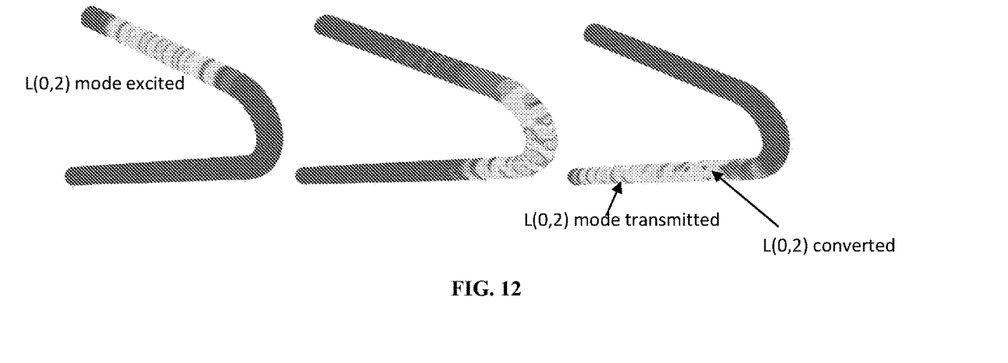
FIG. 12 shows snapshots of the contour of total displacement magnitude at different time instances for 30 degree bend pipe.
Figure 13:
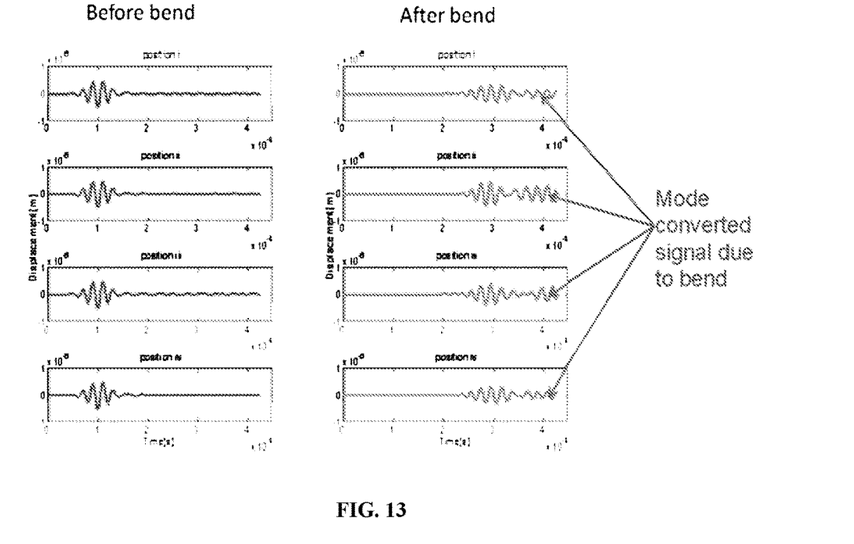
FIG. 13 shows amplitude of axial displacement for 30 bend pipe obtained from the FE simulation.
Figure 14:
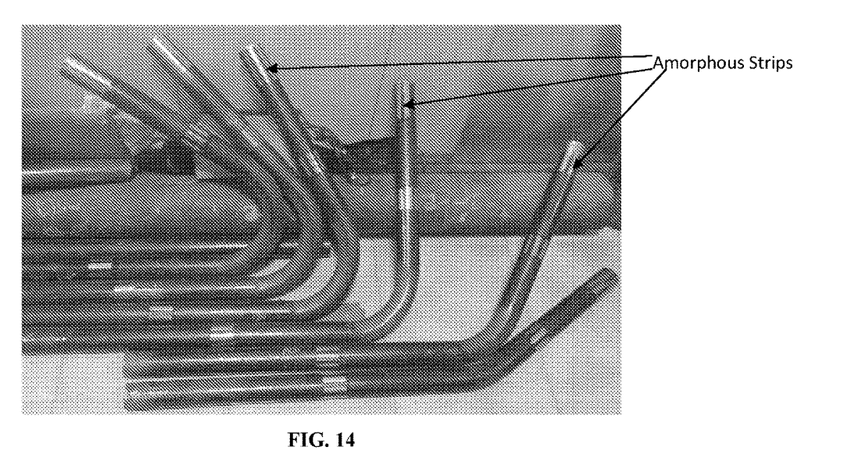
FIG. 14 shows amorphous segmented strips on all bend pipes for the sensor according to aspects of the present disclosure.
Figure 15:
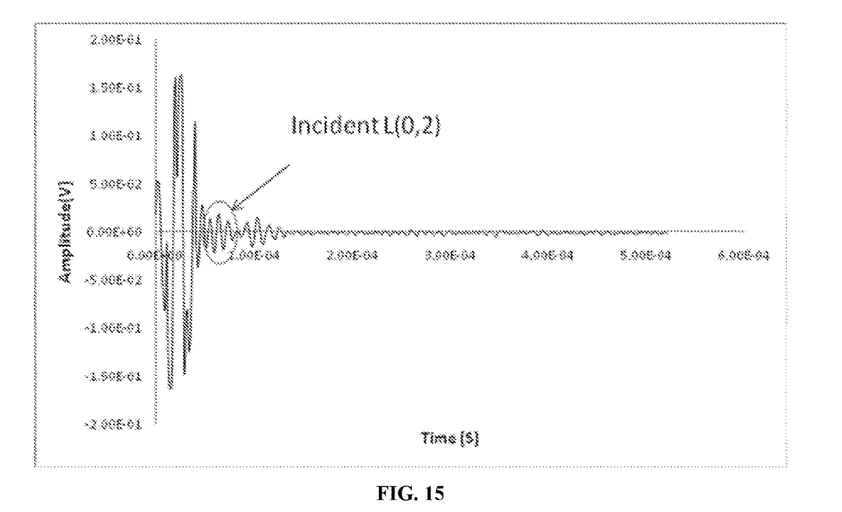
FIG. 15 shows signals obtained from the MsS Sensor technique according to aspects of the present disclosure.
Figure 16:
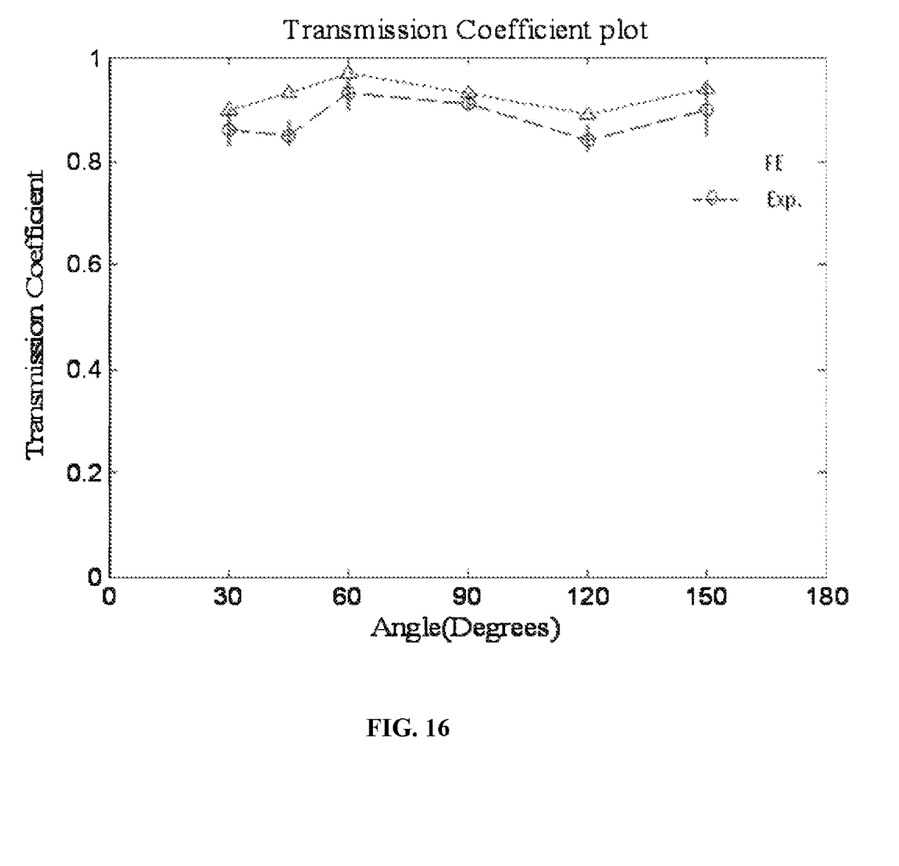
FIG. 16 shows comparison between transmission coefficients obtained from experiments and FE simulation.

This new technique was used to validate a theory for detecting bend pipes. Referring to FIGS. 12 and 13, the simulations were carried out before [3] and it was proposed that only beds with 30° bend radius can do a mode conversion such that it can be detected by a sensor. Other bend angles cannot do such high mode conversion. Using Simulations in ABAQUS/EXPLICIT the author plotted a graph for transmission coefficient (FIG. 16). This graph was validated using the new sensor and it was found that experimental data correlates with the simulation data within experimental errors. Also the transmission coefficient was calculated and was plotted against bend angle. Referring to FIGS. 14 and 15, experiments were carried out for almost all bend angles and data was plotted along with the simulation data. It was observed that there was an agreement between the experimental data and the simulation data. This proves that the new technique for MsS Sensor can be used to detect bends in pipes too.

From the above presented graph it can be seen clearly that the experiments with the new technique complements the simulation results so generated. Therefore, it can be established that the new technique can also be used to detect severe bends in industries. With careful analysis these bends can be differentiated from defects.

Therefore, the capability of the sensor was tested and verified for detecting common defects like circumferential and notch (corrosion) defects. The sensor was also tested at high temperatures and was found to perform well. Lastly, the sensor was used to detect bends in pipes and was found to work well. Therefore, the novel technique has multifold capabilities and can be used for various purposes, without much modification in the design.

Although the invention has been described in terms of examples, it is not limited thereto. Rather, the application should be construed broadly, to include other variants and embodiments of the invention, which may be made by those skilled in the art without departing from the scope and range of equivalents of the invention. One or more features from any embodiment may be combined with one or more features of any other embodiment without departing from the scope of the invention. It will be further understood that the terms "comprises," "comprising," "includes" and/or "including" when used in this specification, specify the presence of stated features, steps, operations, elements, and/or components, but do not preclude the presence or addition of one or more other features, steps, operations, elements, components, and/or groups thereof.

The invention claimed is:

1. A pipeline inspection system, with a magnetostrictive sensor configured to be placed in contact with a pipeline, comprising of:—
   (a) a hollow base cylindrical platform adapted to be around a pipe thereby having generally a matching geometry of the pipe,
   (b) a plurality of segmented ultra sound magnetostrictive strips securely arranged, circumferentially, within the platform for generating in a pipewall a plurality of ultrasonic guided pure mode waves which is either longitudinal mode or a torsional mode,
   (c) a plurality of coils which are wound encircling around the platform, the coils including a first excitation signal coil, a second reflection signal coil and a third DC bias coil magnetizing the pipe, wherein the platform, the strips and the coils co-operatively work as a sensor, and
   (d) a data acquisition system with circuitry for determining and identifying a flaw in the pipe on the basis of received signals from the sensor.

2. The system of claim 1, wherein the three coils are arranged side-by-side juxtaposition along the platform and in spaced relationship.

3. The system of claim 1, wherein the three coils are arranged concentrically layered on top of each other around the platform with an insulation layer in between.

4. The system in claim 1, comprising further a plurality of segmented magnetostrictive strips arranged circumferentially around the pipe, some orienting longitudinally along a pipe axis and some arranged around the pipe perpendicularly to the pipe axis.

5. The system in claim 1, comprising further a plurality of segmented sensor strips arranged circumferentially all orienting longitudinally along a pipe axis.

6. The system in claim 1, comprising further a plurality of longitudinal sensor strips arranged circumferentially all orienting perpendicularly to a pipe axis and wound encircling around the pipe.

7. The system of claim 1, wherein the segmented ultra sound magnetostrictive strips are made of amorphous material having a very steep magnetostrictive curve.

8. The system in claim 7, wherein the amorphous material is Fe with alloys of B and Si.

9. The system in claim 1, wherein the strips are additionally held in position on the platform with roll-on conventional tape capable of withstanding high temperature.

* * * * *